United States Patent [19]

Atkinson

[11] Patent Number: 5,647,852
[45] Date of Patent: Jul. 15, 1997

[54] LAVAGE SYSTEM INCLUDING A CASSETTE ASSEMBLY

[75] Inventor: Robert W. Atkinson, Dover, Ohio

[73] Assignee: Zimmer, Inc., Warsaw, Ind.

[21] Appl. No.: 382,302

[22] Filed: Jan. 31, 1995

[51] Int. Cl.[6] .................................................. A61M 1/00
[52] U.S. Cl. ............................ 604/151; 604/154; 604/34; 417/360
[58] Field of Search ........................... 604/27, 30–35, 604/50, 118, 151–153, 200, 250, 317, 319, 154; 128/DIG. 12, DIG. 13; 417/476, 360, 412

[56] References Cited

U.S. PATENT DOCUMENTS

| | | | |
|---|---|---|---|
| 4,324,532 | 4/1982 | Knife | 417/360 |
| 4,465,474 | 8/1984 | Mardorf et al. | 604/154 |
| 4,561,431 | 12/1985 | Atkinson | 128/66 |
| 4,627,833 | 12/1986 | Cook | 604/34 |
| 4,635,621 | 1/1987 | Atkinson | 128/66 |
| 4,657,490 | 4/1987 | Abbott | 417/478 |
| 4,713,051 | 12/1987 | Steppe et al. | 604/30 |
| 4,755,168 | 7/1988 | Romanelli et al. | 604/34 |
| 4,770,632 | 9/1988 | Ryder et al. | 433/28 |
| 4,790,816 | 12/1988 | Sundblom et al. | 604/31 |
| 4,798,589 | 1/1989 | Tseo | 604/152 |
| 4,818,190 | 4/1989 | Pelmulder et al. | 417/360 |
| 4,820,265 | 4/1989 | DeSatnick et al. | 604/30 |
| 4,940,457 | 7/1990 | Olson | 604/30 |
| 5,019,038 | 5/1991 | Linden | 604/49 |
| 5,030,202 | 7/1991 | Harris | 604/27 |
| 5,041,096 | 8/1991 | Beauchat et al. | 604/118 |
| 5,106,366 | 4/1992 | Steppe | 604/30 |
| 5,125,891 | 6/1992 | Hossain et al. | 604/34 |
| 5,139,484 | 8/1992 | Hazon et al. | 604/154 |
| 5,154,499 | 10/1992 | Atkinson et al. | 312/244 |
| 5,176,646 | 1/1993 | Kuroda | 604/154 |
| 5,195,960 | 3/1993 | Hossain et al. | 604/34 |
| 5,237,309 | 8/1993 | Frantz et al. | 340/679 |
| 5,267,956 | 12/1993 | Beauchat | 604/30 |
| 5,282,787 | 2/1994 | Wortrich | 604/30 |
| 5,295,825 | 3/1994 | Betush | 433/28 |
| 5,338,194 | 8/1994 | Strohmaier | 433/82 |
| 5,364,342 | 11/1994 | Beuchat et al. | 604/30 |
| 5,403,277 | 4/1995 | Dodge et al. | 604/30 |
| 5,460,490 | 10/1995 | Carr et al. | 604/30 |
| 5,470,312 | 11/1995 | Zanger et al. | 604/34 |
| 5,484,402 | 1/1996 | Saravia et al. | 604/35 |

*Primary Examiner*—Corrine M. McDermott
*Assistant Examiner*—Chalin Smith
*Attorney, Agent, or Firm*—Todd A. Dawson

[57] ABSTRACT

The invention is directed to a cassette assembly for use in a medical, dental or therapeutic lavage system, including a cassette housing and a pump disposed within the housing. The pump has an inlet and an outlet, with the inlet and outlet being attachable to a tubing set. The pump is attachable to and driveable by a motor disposed outside the cassette housing. A pressure sensing device disposed within the cassette housing senses a fluid pressure within the outlet.

2 Claims, 4 Drawing Sheets

LAVAGE SYSTEM INCLUDING A CASSETTE ASSEMBLY

BACKGROUND OF THE INVENTION

1. Field of the Invention.

The present invention relates to a lavage system, and, more particularly, to a lavage system having a pump driven by a linear motor.

2. Description of the Related Art.

Lavage systems for irrigation, pulsatile lavage and aspiration are known in the art. For example, U.S. Pat. Nos. 4,561,431 (Atkinson '431) and 4,655,197 (Atkinson '197) each disclose a lavage system having a control unit including a housing in which is disposed a linear motor. The linear motor includes a drive member which extends into a lavage/irrigation pump enclosure. The pump enclosure has a hinged door which may be opened and closed so that a lavage/irrigation pump may be placed within the pump enclosure. The pump consists of a piston pump having a piston rod which attaches to the drive member when the pump is disposed within the pump enclosure. The pump includes an inlet attached to a supply line and an outlet attached to a pressure line. A feedback line attached by means of a T-coupling to the pressure line is connected to a coupling extending from the housing. The coupling is fluidly connected to a pressure sensing transducer disposed within the housing. Thus, when the pump is disposed within the pump enclosure in an operating position, each of the motor, pump and pressure sensing transducer are disposed within the control unit housing.

A problem with conventional lavage systems is that the motor and pressure sensing transducer are fixedly located within the control unit housing, while the lavage/irrigation pump is initially disposed outside the control unit housing and then placed within the housing. The pump must be separately connected to each of the motor and pressure sensing transducer, thereby requiring extra connectors and time to properly connect the pump to the control unit.

What is needed in the art is a structure which allows connection of lavage/irrigation pump and pressure sensing device to a control unit in a simple, one-step operation, with decreased labor and hardware (e.g., connectors) and increased simplicity and reliability.

SUMMARY OF THE INVENTION

The present invention provides a cassette assembly for use with a lavage system which includes a fluid pump and pressure sensing diaphragm disposed within the cassette housing. The fluid pump is attachable to a motor disposed outside the cassette housing.

The invention comprises, in one form thereof, a cassette assembly for use in a medical, dental or therapeutic lavage system, including a cassette housing and a pump disposed within the housing. The pump has an inlet and an outlet, with the inlet and outlet being attachable to a tubing set. The pump is attachable to and driveable by a motor disposed outside the cassette housing. A pressure sensing device disposed within the cassette housing senses a fluid pressure within the outlet.

An advantage of the present invention is that the pump and pressure sensing device are located within a single housing which may be easily connected with a lavage system control unit.

Another advantage is that the control unit housing does not need to be opened to connect the pump with the motor.

Yet another advantage is that the cassette assembly may further include a device for providing an indication to the control unit of an operating pressure within the outlet of the pump.

A further advantage is that the cassette may be connected to the control unit housing at about the same time that the pump is connected to the motor.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
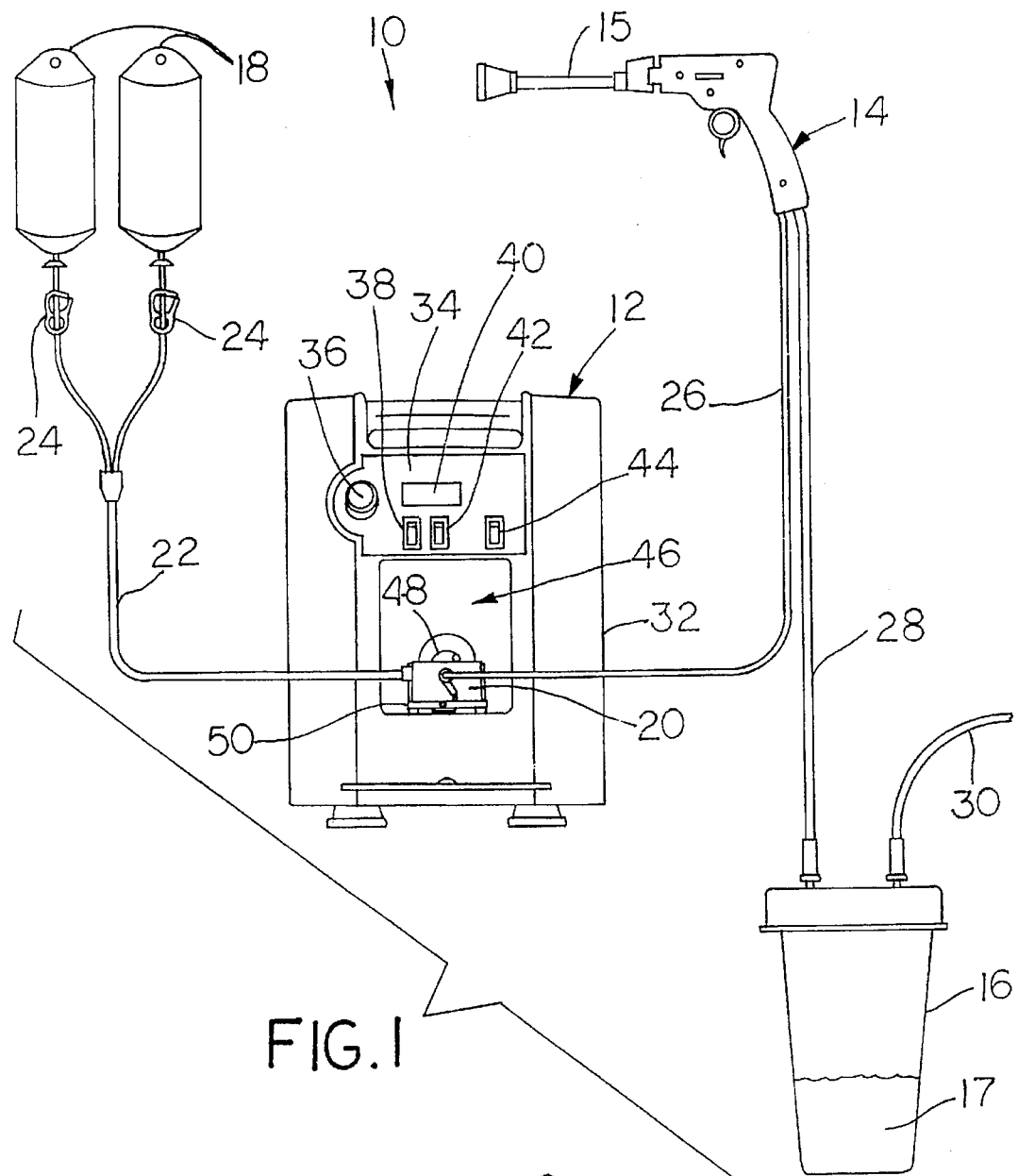
FIG. 1 is a schematic view of one embodiment of a system of the present invention.

Referring now to the drawings and particularly to FIG. 1, there is shown lavage system 10 of the present invention, including a control unit 12, handgun 14, waste container 16, fluid bags 18 and cassette assembly 20. A supply line 22 interconnects fluid bags 18 and cassette assembly 20. Supply line 22 is attached to fluid bags 18 via a spiked connection, as is known, and may include one or more clamps 24 to control fluid flow therethrough. A pressure line 26 interconnects cassette assembly 20 and handgun 14; and a suction line 28 interconnects handgun 14 and waste container 16. A vacuum line 30 interconnects waste container 16 and a vacuum source (not shown). Lavage system 10 can be used, e.g., for medical, dental or therapeutic applications.

Handgun 14 includes a debridement tip 15 which is fluidly connected to each of pressure line 26 and suction line 28 in known fashion. In particular, debridement tip 15 includes a generally coaxial tube arrangement therein in which pressurized fluid is pumped through the inner tube (which is connected to pressure line 26) and exudate is evacuated through the annular space between the inner and outer tubes (which is connected to suction line 28).

Waste container 16 holds exudate 17 evacuated from handgun 14 through suction line 28. Waste container 16 is a sealed container and is connected to the above-mentioned vacuum source (not shown), such as a connection port in a room of a hospital extending to a vacuum pump.

Control unit 12 includes a housing 32 with a control panel 34 affixed thereto. Control panel 34 carries a pressure control knob 36, load/unload switch 38, display 40, run/stop switch 42 and ON/OFF switch 44, each of which will described in further detail under the description of operation, infra. Housing 32 also includes a recess 46 in which is disposed a motor 48 and cassette platform 50 (FIGS. 6–9). More particularly, a frame 52 (FIGS. 6–9) is mounted to housing 32, such as by fasteners (not shown) passing through openings 54.

Figure 6:
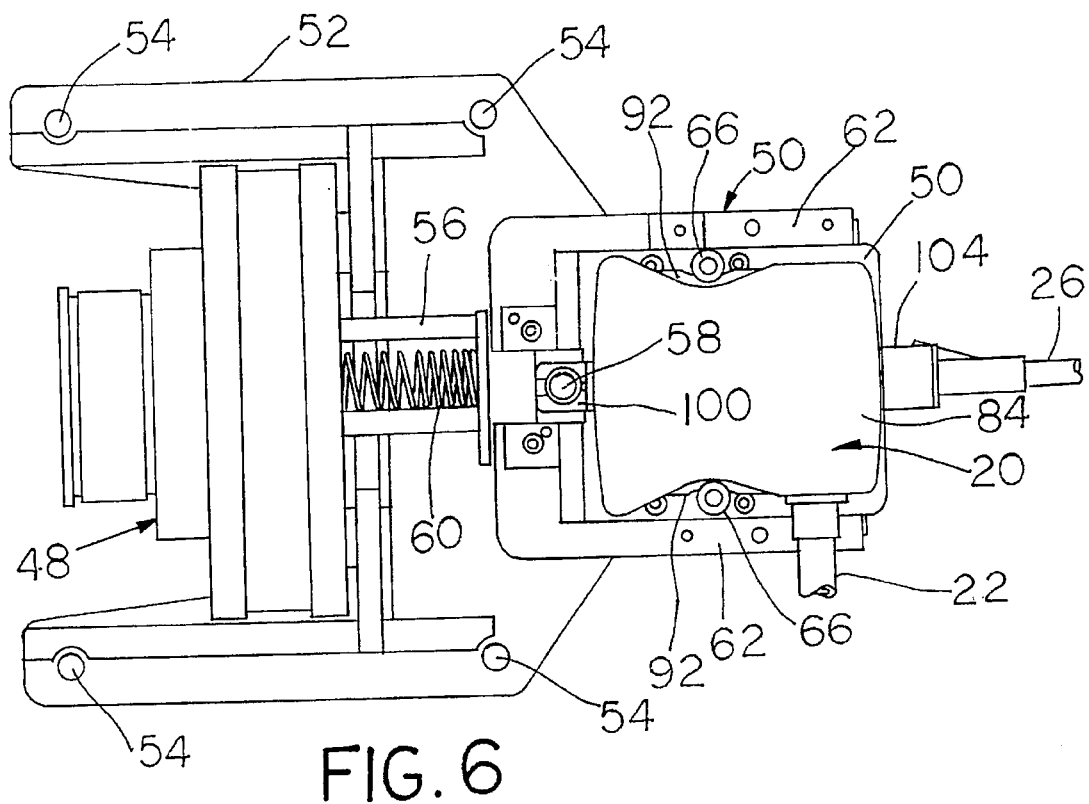
FIG. 6 is a top view of the cassette assembly when mounted to the cassette platform and motor.

Motor 48 is attached to frame 52 and includes a reciprocating drive member 56 having a hook 58. Details of such a motor are disclosed, e.g., in U.S. Pat. No. 4,555,645 (Atkinson '645). In general, drive member 56 of motor 48 is biased to a neutral position by a pair of opposing coil springs, one of which is shown in FIGS. 6–8 and referenced as number 60.

Figure 2:
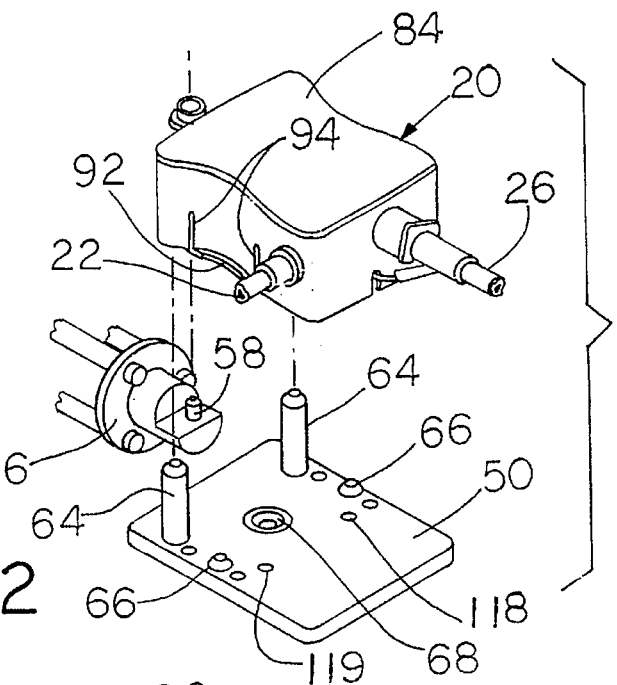
FIG. 2 is an exploded, perspective view illustrating interconnection between one embodiment of the cassette assembly, cassette platform and motor of the present invention.
Figure 7:
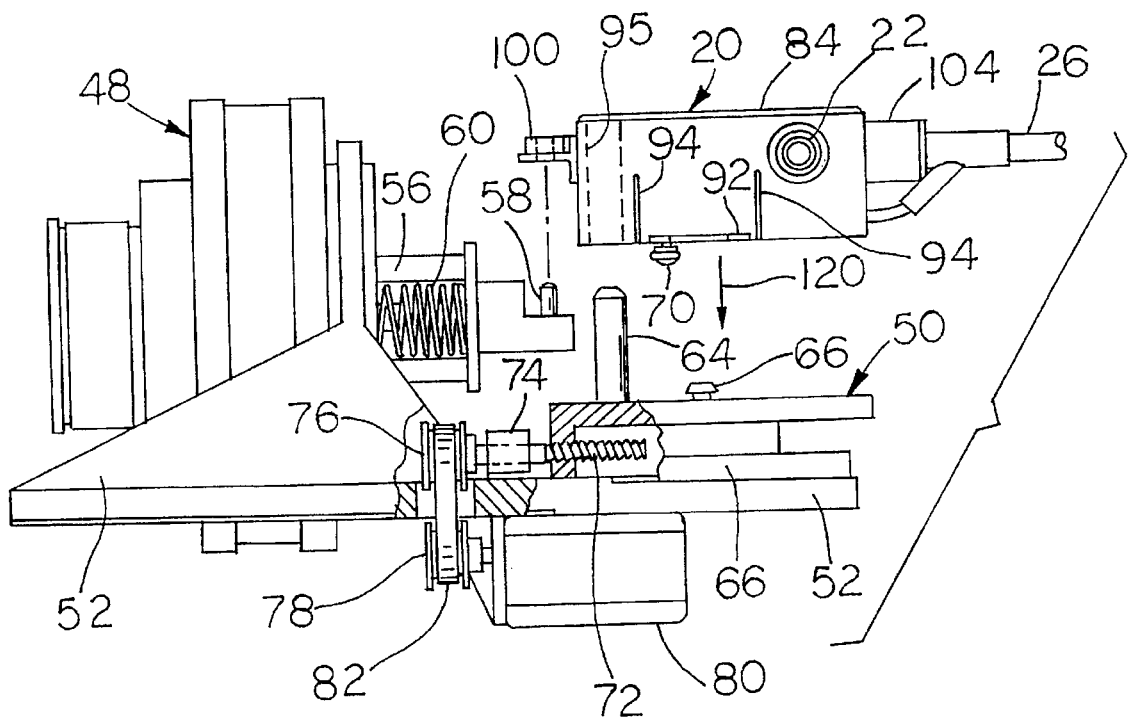
FIG. 7 is a side view illustrating interconnection between the cassette assembly, cassette platform and motor shown in FIG. 2, with the cassette platform shown in the loading position.

Cassette platform 50 is slidably attached to frame 52 (FIGS. 2 and 6–9). Brackets 62 are affixed to frame 52 and slidably receive cassette platform 50. Extending upwardly from cassette platform 50 are a pair of alignment pins 64 for aligning cassette assembly 20 (FIGS. 2 and 7). Also extending upwardly from cassette platform 50 are a pair of locking tabs 66 which function to lock cassette platform 50 with cassette assembly 20. Cassette platform 50 also includes a female connector 68 (FIGS. 2 and 4) which mates with a corresponding male connector 70 formed in cassette assembly 20. Female connector 68 is connected to display 40, such as by a pressure sensing transducer and electrical circuitry disposed within control unit 12 (not shown), for displaying a fluid pressure within female connector 68. For details of such circuitry, reference is made, e.g., to Atkinson '431, described supra.

Figure 8:
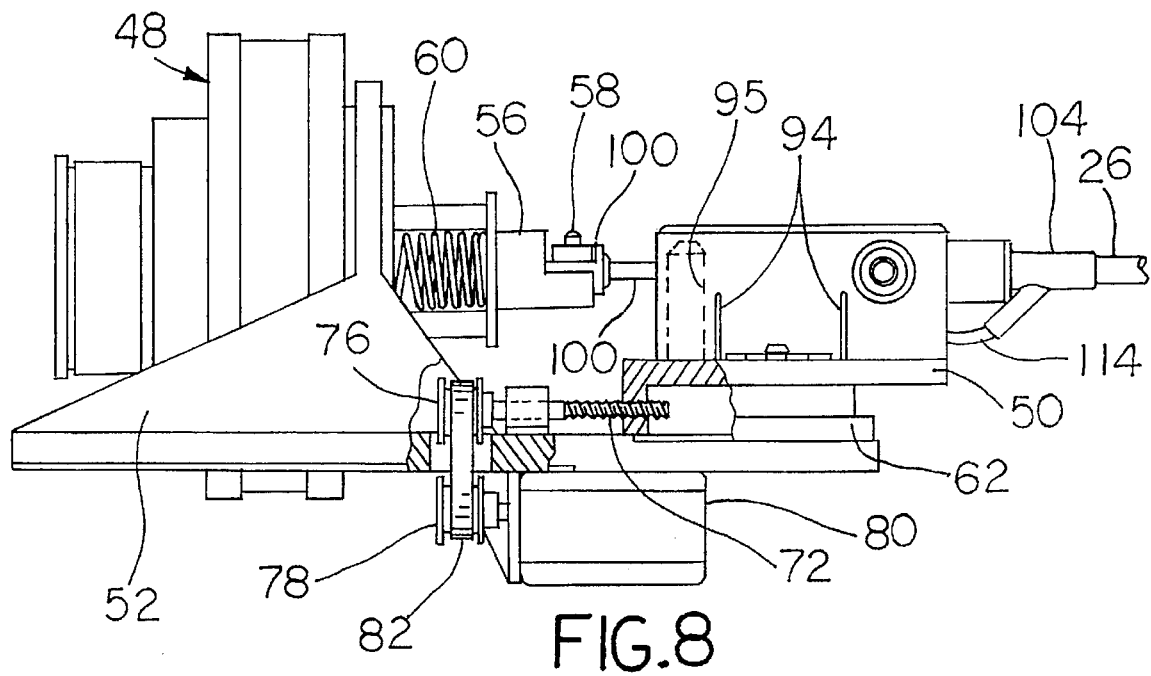
FIG. 8 is a side view of the cassette assembly, cassette platform and motor shown in FIG. 7, with the cassette assembly installed on the cassette platform and the cassette platform in the operating position.
Figure 9:
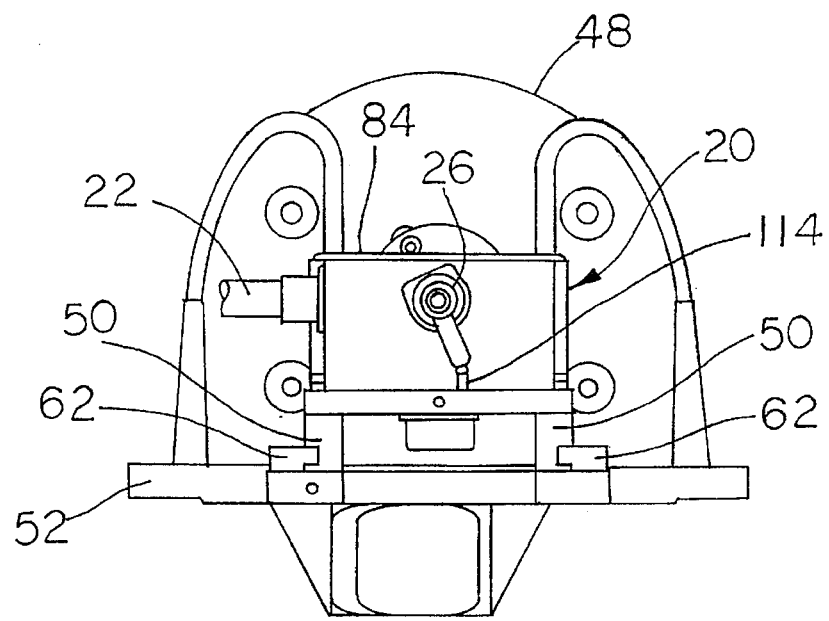
FIG. 9 is an end view of the cassette assembly, cassette platform and motor shown in FIG. 8.

Referring now to FIGS. 7 and 8, the sliding interrelationship between cassette platform 50 and frame 52 is further illustrated. As shown, cassette platform 50 is threadingly connected to a lead screw 72 which is rotatably supported at an opposing end by a bearing 74 which is affixed to frame 52. Lead screw 72 is preferably a triple-lead screw. Affixed to lead screw 72 is a pulley 76 which is interconnected to a pulley 78 of a rotating motor 80 via a belt 82. Rotation of pulley 78 of motor 80 causes rotation of lead screw 72, which in turn causes sliding movement between cassette platform 50 and frame 52.

Referring now to FIGS. 2–9, an embodiment of the cassette assembly 20 of the present invention will be described in greater detail. Cassette assembly 20 includes a cassette housing 84, pump 86, pressure sensing device and maximum threshold operating pressure indicating device.

Cassette housing 84 has an open bottom below which extends male connector 70 of pressure sensing device 88 for interconnection with female connector 68 of cassette platform 50. Side flanges 92 disposed on each side of cassette housing 84 provide a snap-fit with locking tabs 66 on cassette platform 50. Notches 94 in housing 84 are disposed adjacent to side flanges 92 and allow for local deflection of side flanges 92 when initially engaging with locking tabs 66. Cassette housing 84 also includes an alignment device defined by recesses 95 which extend upwardly from the bottom of cassette housing 84 and which are adapted to receive alignment pins 64 therein.

Pump 86 is a piston pump having a reciprocating piston 96 attached to a piston rod 98. Piston 96 is positioned within a cylinder 99 having an inlet 102 and an outlet 104. Piston 96 carries a pair of O-ring seals 97 for sealing engagement with the inner wall of cylinder 99. Inlet 102 and outlet 104 are attached to supply line 22 and pressure line 26, respectively. Disposed within inlet 102 and outlet 104 are a pair of respective poppet-type valves 106 defined by a plunger 108 which is biased to a closed position by a spring 110. Poppet-type valves 106 provide one-way fluid flow through each of inlet 102 and outlet 104, as is apparent in FIG. 3.

Figure 5:
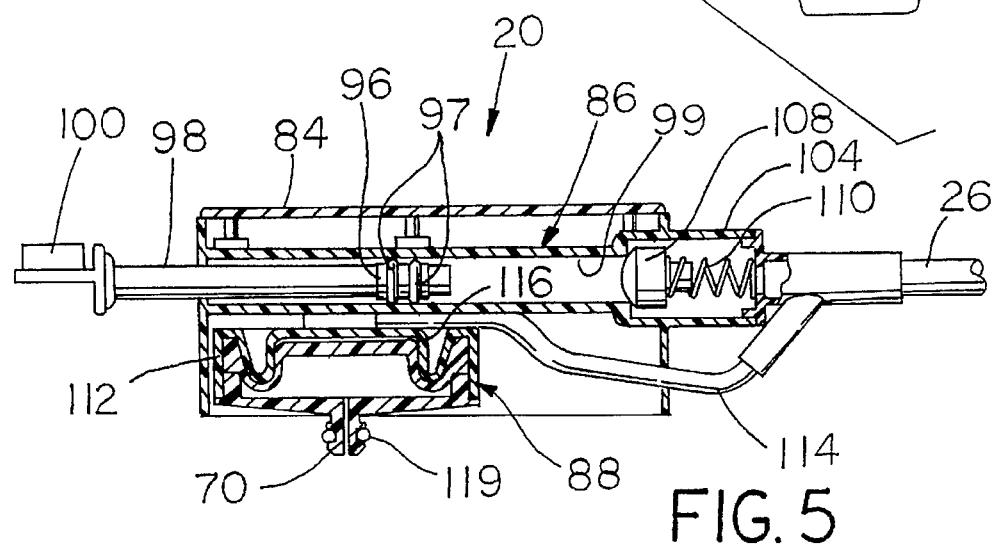
FIG. 5 is a sectional view taken along line 5—5 in FIG. 3.
Figure 3:
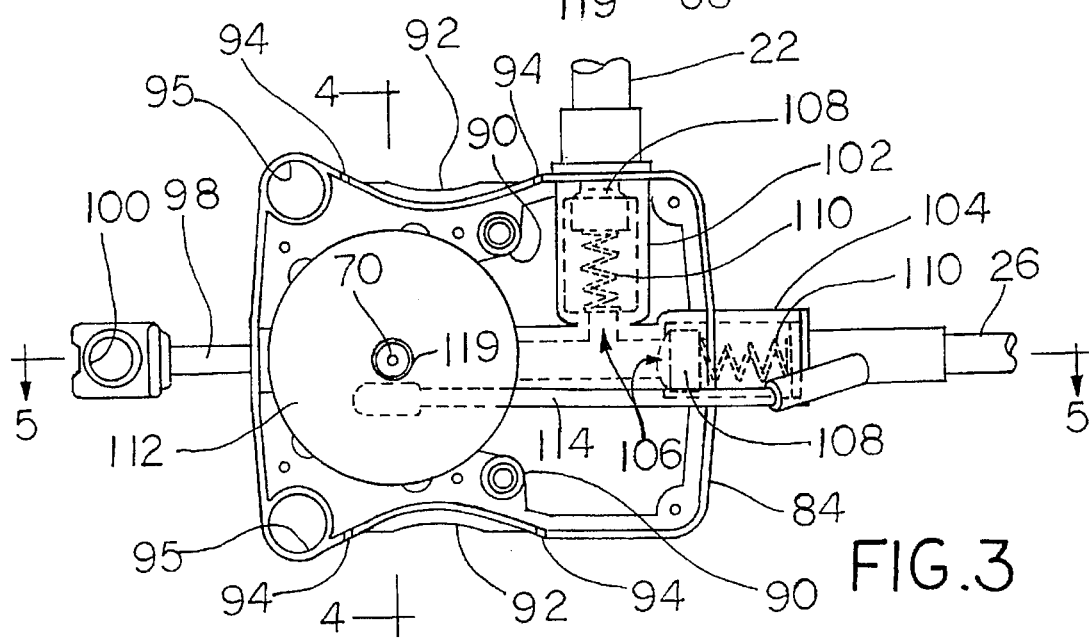
FIG. 3 is a bottom view of the cassette assembly shown in FIGS. 1 and 2.

Piston rod 98 includes an eye portion 100 disposed at a distal end thereof which is opposite to piston 96. Eye portion 100 is sized to receive hook 58 of drive member 56, thereby providing attachment between piston rod 98 and motor 48. Piston rod 98 is shown in a loading position in FIGS. 6 and 7, whereby piston rod 98 is substantially entirely disposed within cylinder 99; and subsequently in an operating position as shown in FIGS. 3, 5 and 8, whereby a portion of piston rod 98 extends from cylinder 99 and piston rod 98 is free to oscillate in reciprocating fashion within cylinder 99.

Figure 4:
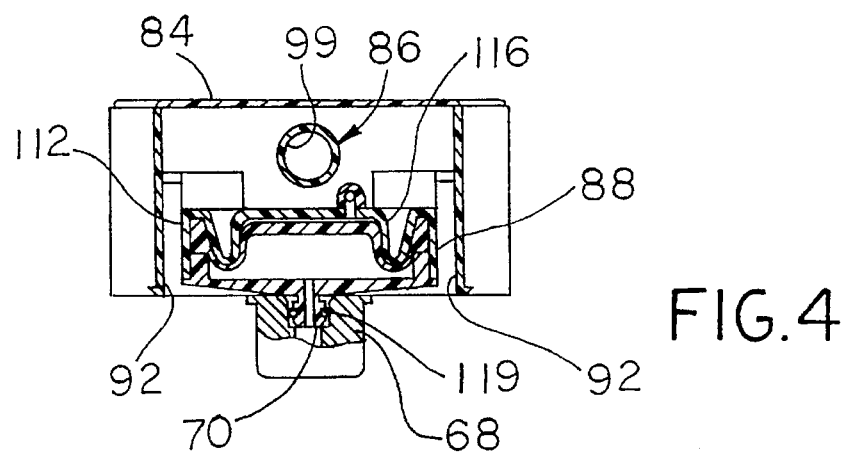
FIG. 4 is a sectional view taken along line 4—4 in FIG. 3.

Pressure sensing device is a diaphragm valve including a case 112 which is fluidly connected with outlet 104 via a feedback line 114. Disposed within case 112 is a diaphragm 116 which is responsive to pressure within case 112. Male connector 70 extends downwardly from case 112 and is received within female connector 68 when cassette assembly 20 is in an installed position on cassette platform 50 (FIG. 4). Male connector 70 includes an annular groove in which is disposed an O-ring seal 119 providing sealing engagement between male connector 70 and female connector 68.

Maximum threshold operating pressure indicating device (FIG. 3) includes a pair of magnets which are disposed within cassette housing 84. Magnets 90 provide a signal which is received by sensors 118 (FIG. 2) disposed in cassette platform 50. More particularly, magnets 90 are carried by cassette housing 84 at two predetermined locations. The presence or nonpresence of each magnet 90 at the respective predetermined locations thus either actuates or fails to actuate a corresponding sensor 118 when cassette assembly 20 is in the installed position on cassette platform 50. Magnets 90 therefore provide a binary signal to control unit 12 depending on the actuated state of sensors 118; namely, OFF/OFF, OFF/ON, ON/OFF and ON/ON. Of course, it is possible to provide additional magnets within cassette housing 84 and corresponding additional sensors within cassette platform 50, thereby increasing the number of possible binary combinations provided to control unit 12. The binary signals provided by magnets 90 indicate an operating pressure within outlet 104, such as a normal operating pressure or a maximum threshold operating pressure.

To operate lavage system 10, ON/OFF switch 44 is turned to the ON position to energized control unit 12. Run/stop switch 42 is left in the OFF position such that linear motor 48 is not energized. When in the OFF position, drive member 56 of motor 48 is biased to a neutral, load position by springs 60. Load/unload switch 38 is then depressed to move cassette platform 50 to the load position shown in FIG. 7. Load/unload switch 38 actuates motor 80 which in turn rotates lead screw 72 and slides cassette platform 50 to the load position. In the load position, cassette platform 50 is positioned such that alignment pins 64 are received within recesses 95 and hook 58 is received within eye portion 100. That is, cassette platform 50 is positioned such that there is simultaneous alignment between alignment pins 64 and recesses 95, and hook 58 and eye portion 100. Cassette assembly 20 is then moved in the downward direction indicated by directional arrow 120 (FIG. 7) such that alignment pins 64 are received within recesses 95 and hook 58 is received within eye portion 100 (FIGS. 6 and 8). Locking tabs 66 snap over side flanges 92 of cassette housing 84 and hold cassette assembly 20 in place.

When cassette assembly 20 is attached to cassette platform 50, magnets 90 actuate sensors 118 (FIG. 2) and provide a signal to control unit 12 indicating that cassette assembly 20 is in place. Optionally, as indicated above, magnets 90 can also be used to provide a signal indicating an operating pressure and/or maximum operating pressure (maximum threshold pressure) within outlet 104 and pressure line 26. Upon actuation of sensors 118, control unit 12 actuates motor 80 which in turn rotates lead screw 72 and moves cassette platform 50 to an operating position in which piston rod 98 is free to oscillate within cylinder 99 (FIG. 8). When in the load position, cassette platform 50 is positioned substantially within recess 46 of housing 32; and when in the operating position, cassette platform 50 is positioned substantially outside recess 46 of housing 32.

Run/stop switch 42 is then depressed to actuate linear motor 48 and reciprocate piston rod 98 within cylinder 99, thereby effecting pressurization of fluid within outlet 104. As piston rod 98 reciprocates, fluid is drawn into cylinder 99 through inlet 102 and is discharged from cylinder 99 through outlet 104. Diaphragm valve 88 provides an indication of the operating pressure within outlet 104 at display 40, which pressure can be adjusted using pressure control knob 36.

To remove cassette assembly 20 from control unit 12, the above-described procedure is essentially reversed.

In the embodiment described above, magnets 90 provide a signal to control unit 12 when cassette assembly 20 is attached to cassette platform 50, and control unit 12 automatically moves cassette platform 50 to the operating position. However, it is to be understood that magnets 90 can be eliminated and cassette platform 50 manually moved to the operating position, such as by depressing load/unload switch 38 a second time to manually actuate motor 80 and move cassette platform 50.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A lavage system comprising:

a frame;

a linear motor mounted to said frame and having a drive member extending outwardly from said motor, said drive member being shiftable between first and second positions in response to said motor, a cassette platform mounted to said frame and being selectively movable to said motor and said drive member, a cassette assembly including a cassette housing, said cassette housing being mountable on said cassette platform, said cassette housing further including a pump having a pump shaft and defining an inlet and an outlet, said cassette assembly further including a pressure sensing diaphragm valve fluidly connected to said pump outlet, said pump shaft being shiftable between first and second positions to force fluid from said inlet to said outlet, said pump shaft being connected to said driver member such that as said driver member shifts toward its first position, said pump shaft shifts toward its first position, said cassette platform being shiftable between a first and second position, wherein with said platform in its first position and the pump shaft in its first position and the driver member in a position between its first and second positions, the cassette assembly pump shaft can be connected to the driver member and the cassette assembly can be connected to the cassette platform, wherein after said cassette assembly is connected to said cassette platform and said driver member, said cassette platform is shifted into its second position wherein said pump shaft is held in a position between its first and second positions until said motor is activated.

2. The system of claim 1 further including a maximum operating pressure sensing device disposed within said cassette assembly and a controller carried by said frame, wherein said maximum operating pressure sensing device communicates with said controller to set a maximum output pressure for the pump.

\* \* \* \* \*